United States Patent [19]

Major

[11] 4,308,013
[45] Dec. 29, 1981

[54] THERMOELECTRIC DIAGNOSTIC INSTRUMENT

[76] Inventor: Emery Major, 1210 Brickyard Cove Rd., Point Richmond, Calif. 94801

[21] Appl. No.: 160,973

[22] Filed: Jun. 19, 1980

[51] Int. Cl.³ .............................................. A61C 3/00
[52] U.S. Cl. .......................................... 433/32; 62/3;
128/742; 219/241
[58] Field of Search ...................... 433/32; 62/3, 293;
128/742, 399, 303.1, 401; 219/241

[56] References Cited

U.S. PATENT DOCUMENTS

| Re. 26,276 | 10/1967 | Hirschhorn | 128/399 |
|---|---|---|---|
| 2,200,321 | 5/1940 | Angell | 433/32 |
| 2,454,576 | 11/1948 | Slack | 219/241 |
| 3,130,553 | 4/1964 | Makow | 62/3 |
| 3,207,159 | 9/1965 | Tateisi | 62/3 |
| 3,274,995 | 9/1966 | Eidus | 433/32 |
| 3,533,397 | 10/1970 | Scher | 128/742 |
| 3,618,590 | 11/1971 | Yardley et al. | 128/303.1 |
| 3,971,229 | 7/1976 | Privas | 62/3 |
| 4,249,899 | 2/1981 | Davis | 433/32 |

OTHER PUBLICATIONS

"Thermal Pulp Testing", Cooley et al., General Dentistry, June 1978, pp. 58 and 60.

Primary Examiner—Gene Mancene
Assistant Examiner—John J. Wilson
Attorney, Agent, or Firm—Thomas R. Lampe

[57] ABSTRACT

A thermoelectric diagnostic instrument including a housing, a thermocouple device in the housing and thermoconductor means for delivering heat and cold from the thermocouple device to contact elements located externally of the housing. Heat dissipating means including a heat sink for receiving excess heat from the thermocouple device and means for directing ambient air into engagement with the heat sink is also located in said housing.

12 Claims, 6 Drawing Figures

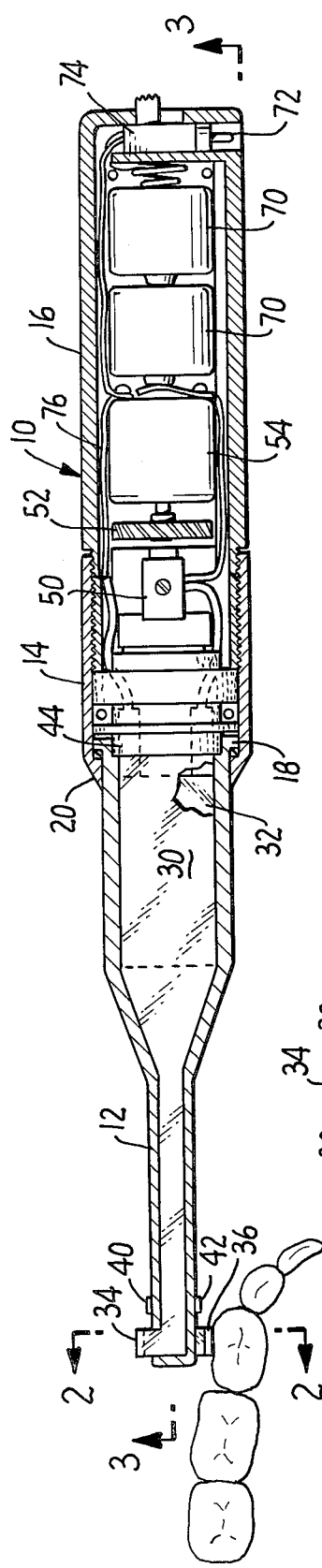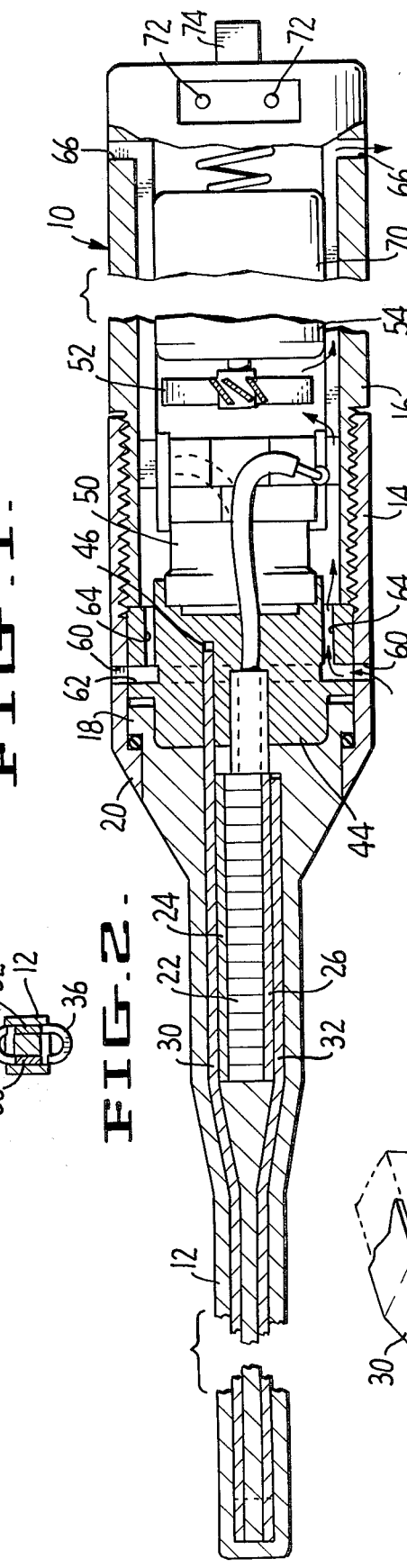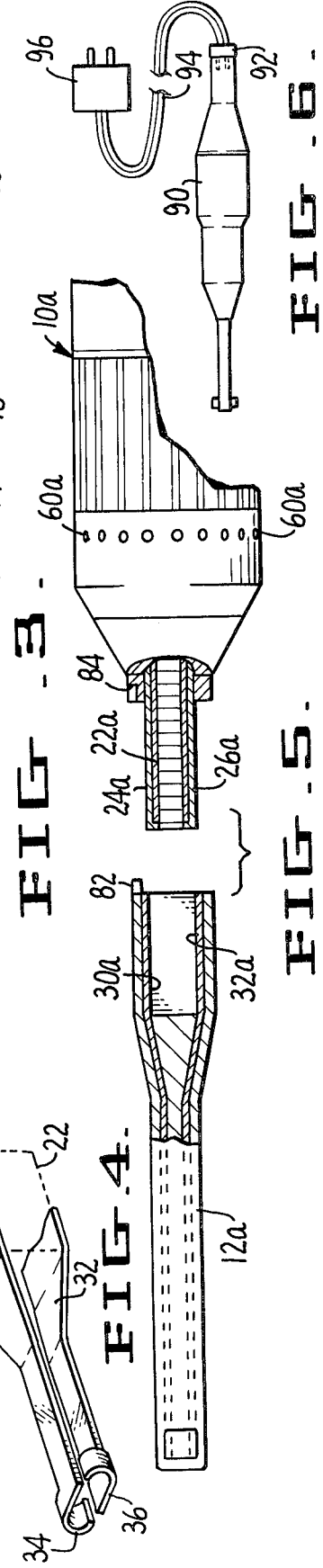

THERMOELECTRIC DIAGNOSTIC INSTRUMENT

BACKGROUND OF THE INVENTION

1. Field of the Invention

This invention relates to diagnostic instruments and more particularly to a thermoelectric instrument for applying heat and cold to small selected portions of the patient's body. The device finds particular application as a dental pulp tester.

2. Description of the Prior Art

A diagnostic procedure often employed in dentistry is that of thermal pulp testing wherein the temperature of a tooth is either raised or lowered by the application of heat or cold. Conventionally used pulp testing procudures, such as those described in an article entitled "Thermal Pulp Testing" commencing on page 58 of the May/June, 1978 issue of *General Dentistry* magazine, are often inconvenient, time consuming, messy and potentially harmful to the patient. As a consequence, several attempts have been made in the past to design instruments specifically adapted for applying heat or cold to a localized area of the body such as a tooth surface. Examples of such instruments are shown in the following patents: Eidus U.S. Pat. No. 3,274,995 issued Sept. 27, 1966; Scher U.S. Pat. No. 3,533,397 issued Oct. 13, 1970; Crump et al U.S. Pat. No. 3,575,176 issued Apr. 20, 1971; Frank et al U..S. Pat. No. 3,618,590 issued Nov. 9, 1971; and Foti U.S. Pat. No. 4,143,649 issued Mar. 13, 1979.

A major difficulty in the prior art, especially with respect to those devices employing mechanisms utilizing the Peltier effect, has been the efficient dissipation of excess heat build-up. The complex and voluminous heat exchange systems and heat sinks thus far employed in an attempt to solve this problem has limited acceptance of such devices.

SUMMARY OF THE INVENTION

The purpose of the present invention is, therefore, to provide a compact, self contained diagnostic instrument for applying both heat and cold to localized areas which incorporates an efficient system for dissipating excess heat generated by a Peltier module employed therein. Several components of the device contribute to the attainment of this objective; in particular, the employment of insulated thermoconductor elements in operative association with the hot and cold junction plates of a Peltier device to deliver heat and cold to contact elements positioned externally of a housing accommodating said Peltier device, heat sink means operatively associated with the hot junction plate of said Peltier device, and a motor driven fan for drawing ambient air into the interior of said housing into contact with the heat sink means and out of the housing.

Other features, advantages and objects of the present invention will become apparent with reference to the following detailed description and accompanying drawings in which:

DESCRIPTION OF DRAWINGS

FIG. 1 is a side elevational sectional view of an instrument constructed according to the teachings of the present invention;

FIG. 2 is a sectional view taken along line 2—2 of FIG. 1;

FIG. 3 is an enlarged sectional view taken along line 3—3 of FIG. 1 with portions thereof broken away;

FIG. 4 is an isometric view illustrating details of the thermoconductor elements and contact elements employed in the embodiment of FIG. 1; and FIGS. 5 and 6 are side elevational views of alternative embodiments of apparatus constructed in accordance with the teachings of the present invention.

DETAILED DESCRIPTION

A preferred form of apparatus constructed in accordance with the teachings of the present invention is shown in FIGS. 1-4, and includes a housing 10 incorporating a cap member 12. Housing 10 additionally comprises two threadedly engaged housing sections 14 and 16. The housing is preferably formed of plastic or other suitable insulating material. Cooperating flanges 18 and 20 at the ends of cap member 12 and section 14, respectively, serve to secure the cap member to the rest of the housing. The cap member may be readily removed from the rest of the housing for cleaning, replacement, etc.

Disposed within the interior of the cap member of housing 10 is thermocouple device 22 utilizing the Peltier effect, said device 22 being hereinafter referred to as the Peltier module. Peltier module 22 includes opposed junction plates 24 and 26. When electrical current is passed through the Peltier module the temperature of one of the plates is lowered and the temperature of the other is raised in a well known manner. In the disclosed arrangement, application of electrical energy to the Peltier module will result in plate 24 being heated and plate 26 being cooled.

Disposed in face to face engagement with plates 24 and 26 are thermoconductor means in the form of thin, elongated strips 30 and 32 of copper or other suitable thermoconductive material which are preferably embedded as shown in the insulating plastic material of cap member 12 so that they are maintained in generally parallel relationship. At the outermost extent of cap member 12, strips 30 and 32 are bent as shown to form curved contact elements 34 and 36 which extend outwardly from the cap member 12 in different directions whereby the contact elements are spaced from one another on opposite sides of the cap member. Contact elements 34 and 36 are preferably gold plated. It will be appreciated that upon actuation of Peltier module 22 heat will be transmitted to contact element 34 by strip 30 and cold will be transmitted to contact element 36 by strip 32. In FIG. 1 contact element 36 is shown in contact with a tooth to impart cold thereto. With a simple twist of the wrist the hot contact element 34 alternatively may be placed in engagement with a tooth. Suitable indicia is preferably provided on the contact elements themselves, or on the cap member, to indicate to the user which contact element is hot and which is cold. For example, red and blue dots 40 and 42 could be applied to the cap member as shown to indicate the hot contact element and cold contact element, respectively.

Disposed adjacent to Peltier module 22 within the interior of housing 10 is a heat sink 44 formed of aluminum or other suitable material. Strip 30 extends beyond junction plate 24 and is positioned in engagement with the heat sink 44 within a slot 46 formed therein as shown whereby excess heat generated by the Peltier module will be absorbed by the heat sink and dissipated thereby. It should be noted that the cap member cannot be properly affixed to the remainder of the housing unless strip 30 is in slot 46, thus insuring that the contact element 34 is always the heated contact element in conformance with the indication provided by indicia 40.

Positioned adjacent to heat sink 44 is a thermostat 50, the function of which will be described below. Adjacent to the thermostat 50 is another component of the heat dissipating mechanism of the present invention, namely, rotary fan 52 driven by electric motor 54. Upon actuation of motor 54 the fan 52 will serve to draw ambient air into the interior of the housing through air ingress apertures 60 formed in the housing about the periphery thereof. The air will flow along a flow path indicated by the arrows in FIG. 3. It will be noted that the flow path is partially defined by the heat sink and in particular by a groove 62 formed in the heat sink which provides communication between apertures 60 and spaced air flow passageways 64 formed in the heat sink. After passing through the heat sink the heated air passes fan 52 and proceeds along the interior of housing 10 until it leaves the housing through air egress apertures 66 formed therein.

The Peltier module 22 and electric motor 54 are powered by batteries 70 positioned within the housing interior. The batteries 70 are preferably of a rechargeable type, such as nickel cadmium batteries, and charger connector pins 72 are provided to permit recharging of the device when it is not in use. Suitable switch means 74 is provided to simultaneously establish electrical communication between the batteries, motor 54 and Peltier module 22 through wiring 76. Thermostat 50 is positioned in the electrical circuit so as to temporarily shut off power to the Peltier module when the heat of heat sink 44 passes a predetermined temperature. The motor 54 will continue to operate as long as switch means 74 is closed however, if it is in parallel with the thermostat as is preferred. FIG. 5 shows an alternative embodiment of the invention, differing from that previously described in that the Peltier module 22a is not removable with cap member 12a when the cap member is disconnected from the rest of housing 10a. Such an arrangement is particularly desirable for autoclaving. To assure correct alignment when the cap member is replaced with strips 30a and 32a in engagement with junction plates 24a and 26a, respectively, suitable alignment means such as a key and slot arrangement 82 and 84 are preferably employed.

FIG. 6 shows yet another alternative embodiment of the invention wherein the instrument 90 has a socket accommodating a removable plug 92 which is in turn connected by cord 94 to a transformer 96 adapted to be plugged into a conventional electrical socket.

I claim:

1. A thermoelectric diagnostic instrument comprising:
    a housing defining an interior;
    a thermocouple device mounted in said housing and having a plurality of junction plates;
    means for selectively inducing an electrical current in said thermocouple device to actuate said thermocouple device whereby at least one junction plate is cooled and at least one junction plate is heated;
    separate thermoconductor elements extending from each of said heated and cooled plates to separate contact elements being adapted for selective contact with a patient; and
    means in said housing for dissipating excess heat generated by said thermocouple device, said heat dissipating means comprising heat sink means positioned in said housing interior and operatively connected to said heated plate and the thermoconductor element extending from said heated plate.

2. The instrument of claim 1 wherein said heat dissipating means additionally comprises a motor driven fan in said housing interior for inducing an air flow within said housing interior along a flow path between air ingress and air egress apertures formed in said housing to provide air flow communication between the housing interior and the ambient atmosphere, said flow path at least partially defined by a passageway in said heat sink means communicating with said air ingress apertures and directed toward said air egress apertures whereby ambient air heated by said heat sink means will be transported by said motor driven fan out of said air egress apertures and away from said heat sink means and thermoconductor operatively associated therewith.

3. The instrument of claim 1 wherein said thermoconductor elements comprise two elongated thin thermoconductor elements and wherein said housing includes a cap member formed of insulating material and releasably secured to the rest of said housing, said thermoconductor elements being positioned within the cap member.

4. The instrument of claim 3 wherein said contact elements are located at the ends of said thermoconductor elements remote from said thermocouple device and project outwardly from said cap member on opposed sides of said cap member at the extremity thereof.

5. The instrument of claim 1 wherein at least one of said thermoconductor elements is in engagement with both the heat sink means and a heated junction plate of said thermocouple device.

6. A thermoelectric diagnostic instrument comprising:
    a housing defining an interior;
    Peltier module means of unitary construction in said housing and having hot and cold junction plates;
    a thermoconductor element in operative engagement with each of said plates for transmitting heat and cold to contact elements spaced from said plates and disposed external of said housing;
    heat sink means positioned in said housing interior for dissipating heat generated by said Peltier module means and operatively connected to said hot plate and the thermoconductor element in operative engagement with said hot plate to draw heat therefrom; and
    means in said housing interior for directing a flow of air past said heat sink means and out of said housing.

7. A thermoelectric diagnostic instrument comprising:
    a housing defining an interior and including a cap member selectively removably connected to the rest of said housing;
    a Peltier module positioned in said housing interior and having hot and cold junction plates;
    a heat sink;
    elongated thermoconductor elements positioned in spaced relationship in said cap member and extending from said Peltier module to a location remote therefrom, one of said elongated thermoconductor elements being operatively connected to said hot junction plate and said heat sink and the other of said elongated thermoconductor elements being operatively connected to said cold junction plate; and contact elements located at the ends of said elongated thermoconductor elements remote from said Peltier module means and projecting outwardly from said cap member at spaced locations thereon.

8. The instrument of claim 7 further comprising means for inducing an air flow within said housing interior along a flow path through said heat sink means.

9. The instrument of claim 7 wherein said cap member is constructed of heat insulating material and wherein said thermoconductor elements comprise metallic strips imbedded in said cap member in spaced relationship to one another.

10. The instrument of claim 7 wherein said contact elements are curved and at least partially formed from said metallic strips and extend outwardly from said cap member at the extremity thereof in opposite directions whereby the contact elements are spaced from one another in opposition.

11. The instrument of claim 7 additionally comprising alignment means for positioning said cap member at a predetermined location relative to the remainder of said housing whereby said thermoconductor elements are always disposed at a predetermined orientation relative to said housing and heat sink.

12. The instrument of claim 11 additionally comprising indicia on said instrument visible to the operator for identifying which of said contact elements is heated and which is cooled by the elongated thermoconductor elements.

* * * * *